(12) United States Patent
Galeotti et al.

(10) Patent No.: US 12,579,740 B2
(45) Date of Patent: Mar. 17, 2026

(54) SYSTEM, METHOD, AND COMPUTER PROGRAM PRODUCT FOR DETERMINING A NEEDLE INJECTION SITE

(71) Applicant: Carnegie Mellon University, Pittsburgh, PA (US)

(72) Inventors: John Michael Galeotti, Pittsburgh, PA (US); Edward Chen, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 173 days.

(21) Appl. No.: 18/284,174

(22) PCT Filed: Mar. 25, 2022

(86) PCT No.: PCT/US2022/021899
§ 371 (c)(1),
(2) Date: Sep. 26, 2023

(87) PCT Pub. No.: WO2022/204485
PCT Pub. Date: Sep. 29, 2022

(65) Prior Publication Data
US 2024/0169666 A1     May 23, 2024

Related U.S. Application Data

(60) Provisional application No. 63/166,312, filed on Mar. 26, 2021.

(51) Int. Cl.
*G06T 17/00* (2006.01)
*A61B 17/34* (2006.01)
(Continued)

(52) U.S. Cl.
CPC .......... *G06T 17/00* (2013.01); *A61B 17/3403* (2013.01); *G06T 7/10* (2017.01); *G16H 30/40* (2018.01)

(58) Field of Classification Search
CPC ............ G06T 7/10; G06T 2207/10028; G06T 2207/30004; G06T 7/55; G06T 19/00;
(Continued)

(56) References Cited

U.S. PATENT DOCUMENTS

| | | | | |
|---|---|---|---|---|
| 11,195,057 B2 * | 12/2021 | Zadeh | .................... | G06N 3/006 |
| 2017/0309081 A1 | 10/2017 | Carmi | | |

(Continued)

FOREIGN PATENT DOCUMENTS

| | | |
|---|---|---|
| KR | 102073162 B1 | 3/2020 |

OTHER PUBLICATIONS

Scheikl PM, Laschewski S, Kisilenko A, Davitashvili T, Müller B, Capek M, Müller-Stich BP, Wagner M, Mathis-Ullrich F. Deep learning for semantic segmentation of organs and tissues in laparoscopic surgery. InCurrent directions in biomedical engineering Sep. 17, 2020 (vol. 6, No. 1, p. 20200016). De Gruyter.*

*Primary Examiner* — Phu K Nguyen
(74) *Attorney, Agent, or Firm* — The Webb Law Firm

(57)     ABSTRACT

Provided is a system, method, and computer program product for determining a needle injection site. The method includes segmenting, with at least one computing device, an image of a sequence of images into at least one object based on a machine-learning model configured to estimate its uncertainty for each segmentation, generating, with the at least one computing device, a 3D model of the at least one object, and determining, with the at least one computing device, an insertion location of the at least one object based at least partially on an output of the machine-learning model.

19 Claims, 6 Drawing Sheets

700

(51) Int. Cl.
    *G06T 7/10*       (2017.01)
    *G16H 30/40*    (2018.01)
(58) Field of Classification Search
    CPC . G06T 7/77; G06T 17/00; G06T 2207/20084;
           G06T 2210/41; G06T 2207/10132; G16H
           20/40; G16H 30/40; G16H 50/20; G16H
           50/70; G16H 50/50; A61B 17/3403;
           A61B 34/10; A61B 2034/107; A61B
           2017/3409
    USPC ........................................................ 345/418
    See application file for complete search history.

(56) References Cited

U.S. PATENT DOCUMENTS

| | | |
|---|---|---|
| 2018/0161502 A1 | 6/2018 | Nanan et al. |
| 2019/0192226 A1* | 6/2019 | Lang ........................ A61F 2/32 |
| 2020/0184278 A1 | 6/2020 | Zadeh et al. |
| 2021/0059762 A1 | 3/2021 | Ng et al. |

* cited by examiner

SYSTEM, METHOD, AND COMPUTER PROGRAM PRODUCT FOR DETERMINING A NEEDLE INJECTION SITE

CROSS REFERENCE TO RELATED APPLICATIONS

This application is the United States national phase of International Application No. PCT/US22/21899, filed Mar. 25, 2022, and claims priority to U.S. Provisional Patent Application No. 63/166,312, filed Mar. 26, 2021, the disclosures of which are hereby incorporated herein by reference in their entireties.

GOVERNMENT LICENSE RIGHTS

This invention was made with United States government support under W81XWH-19-C-0083 awarded by U.S. Army Medical Research Activity. The United States government has certain rights in the invention.

BACKGROUND

1. Field

This disclosure relates generally to image segmentation and, in non-limiting embodiments, to systems, methods, and computer program products for determining a needle injection site.

2. Technical Considerations

Percutaneous (e.g., needle-puncture) procedures are often used for a wide variety of anatomical targets within the body and are typically associated with performing safe and minimally-invasive interventions (including surgeries). Common applications include central vascular access for resuscitation, arterial pressure monitoring, and emergency dialysis catheter placement. Rarer, more invasive applications include endovascular interventions, extra-corporeal membrane oxygenation (ECMO), and resuscitative endovascular balloon occlusion (REBOA). In many of those cases, placement of a needle in the proper location is essential to a positive outcome.

Percutaneous femoral arterial access is associated with serious complications. Especially with older patients, complications related to insertion, such as hematomas (2-8%) and pseudoaneurysms (1-2%), are becoming more common with the growing number of procedures done in the femoral area. The risk of such complications is further increased when dealing with high-tempo, stressful situations or less experienced medical clinicians. Furthermore, inaccurate judgment of remembered knowledge or ultrasound images for guidance often result in multiple punctures, taking more time in critical scenarios. Severe medical issues also arise as a result of needle insertion in other location sites, such as transradial artery and liver access.

SUMMARY

According to non-limiting embodiments or aspects, provided is a method comprising: segmenting, with at least one computing device, an image of a sequence of images into at least one object based on machine-learning model configured to estimate its uncertainty for each segmentation; generating, with the at least one computing device, a 3D model of the at least one object; and determining, with the at least one computing device, an insertion location the at least one object based at least partially on an output of the machine-learning model.

In non-limiting embodiments or aspects, the method further comprises collecting the sequence of images from a subject, each image in the sequence of images having spatial information. In non-limiting embodiments or aspects, wherein determining the insertion location based at least partially on an output of the machine-learning model comprises determining the insertion location based at least partially on the 3D model, the 3D model generated based on the output of the machine-learning model and including having associated uncertainty values based on the output of the machine-learning model. In non-limiting embodiments or aspects, wherein generating the 3D model is based at least partially on the output of the machine-learning model. In non-limiting embodiments or aspects, the machine-learning model is configured to output a predictive mean and a predictive variance. In non-limiting embodiments or aspects, the machine-learning model comprises encoder blocks and decoder blocks, wherein each encoder block and decoder block comprises a convolution layer, a batch normalization layer, and a ReLu layer.

In non-limiting embodiments or aspects, the machine-learning model comprises a dropout layer arranged at an output of each encoder block and decoder block, the dropout layer configured to output a mean and a variance for each encoder block and decoder block. In non-limiting embodiments or aspects, the dropout layer is configured to estimate the mean and the variance based on at least two iterations. In non-limiting embodiments or aspects, wherein generating the 3D model comprises: filtering uncertain segmentation results based on segmentation maps and uncertainty maps output by the machine-learning model. In non-limiting embodiments or aspects, wherein filtering comprises: calculating an average uncertainty value for each segmented object; and filtering by class based on an uncertainty threshold determined based on a predictive mean and a predictive variance output by the machine-learning model. In non-limiting embodiments or aspects, wherein determining the insertion location based on the 3D model comprises: detecting a bifurcation point in the object in the 3D model; detecting a caudal end of a segmented ligament; determining an insertion region between the bifurcation point and the caudal end of the segmented ligament; and determining the insertion location on the object based on a plurality of total site scores generated for different points along the object. In non-limiting embodiments or aspects, the at least one object comprises at least one of the following: arteries, veins, ligaments, nerves, bones, muscle, lesions, foreign bodies, or any combination thereof. In non-limiting embodiments or aspects, the 3D model comprises uncertainty values. In non-limiting embodiments or aspects, wherein a plurality of points on the 3D model correspond to an associated uncertainty value stored external to the 3D model.

According to non-limiting embodiments or aspects, provided is a system comprising at least one computing device programmed or configured to: segment an image of a sequence of images into at least one object based on machine-learning model configured to estimate its uncertainty for each segmentation; generate, a 3D model of the at least one object; and determine an insertion location the at least one object based at least partially on an output of the machine-learning model.

In non-limiting embodiments or aspects, the at least one computing device is further programmed or configured to collect or receive the sequence of images from a subject, each image in the sequence of images having spatial information. In non-limiting embodiments or aspects, wherein determining the insertion location based at least partially on an output of the machine-learning model comprises determining the insertion location based at least partially on the 3D model, the 3D model generated based on the output of the machine-learning model and including having associated uncertainty values based on the output of the machine-learning model. In non-limiting embodiments or aspects, wherein generating the 3D model is based at least partially on the output of the machine-learning model. In non-limiting embodiments or aspects, the machine-learning model is configured to output a predictive mean and a predictive variance. In non-limiting embodiments or aspects, the machine-learning model comprises encoder blocks and decoder blocks, wherein each encoder block and decoder block comprises a convolution layer, a batch normalization layer, and a ReLu layer.

In non-limiting embodiments or aspects, the machine-learning model comprises a dropout layer arranged at an output of each encoder block and decoder block, the dropout layer configured to output a mean and a variance for each encoder block and decoder block. In non-limiting embodiments or aspects, the dropout layer is configured to estimate the mean and the variance based on at least two iterations. In non-limiting embodiments or aspects, wherein generating the 3D model comprises: filtering uncertain segmentation results based on segmentation maps and uncertainty maps output by the machine-learning model. In non-limiting embodiments or aspects, wherein filtering comprises: calculating an average uncertainty value for each segmented object; and filtering by class based on an uncertainty threshold determined based on a predictive mean and a predictive variance output by the machine-learning model. In non-limiting embodiments or aspects, wherein determining the insertion location based on the 3D model comprises: detecting a bifurcation point in the object in the 3D model; detecting a caudal end of a segmented ligament; determining an insertion region between the bifurcation point and the caudal end of the segmented ligament; and determining the insertion location on the object based on a plurality of total site scores generated for different points along the object. In non-limiting embodiments or aspects, the at least one object comprises at least one of the following: arteries, veins, ligaments, nerves, bones, muscle, lesions, foreign bodies, or any combination thereof. In non-limiting embodiments or aspects, the 3D model comprises uncertainty values. In non-limiting embodiments or aspects, wherein a plurality of points on the 3D model corresponds to an associated uncertainty value stored external to the 3D model.

According to non-limiting embodiments or aspects, provided is a computer program product comprising at least one non-transitory computer-readable medium including program instructions that, when executed by at least one computing device, cause the at least one computing device to: segment an image of a sequence of images into at least one object based on machine-learning model configured to estimate its uncertainty for each segmentation; generate, a 3D model of the at least one object; and determine an insertion location the at least one object based at least partially on an output of the machine-learning model.

In non-limiting embodiments or aspects, the at least one computing device is further caused to collect or receive the sequence of images from a subject, each image in the sequence of images having spatial information. In non-limiting embodiments or aspects, wherein determining the insertion location based at least partially on an output of the machine-learning model comprises determining the insertion location based at least partially on the 3D model, the 3D model generated based on the output of the machine-learning model and including having associated uncertainty values based on the output of the machine-learning model. In non-limiting embodiments or aspects, wherein generating the 3D model is based at least partially on the output of the machine-learning model. In non-limiting embodiments or aspects, the machine-learning model is configured to output a predictive mean and a predictive variance. In non-limiting embodiments or aspects, the machine-learning model comprises encoder blocks and decoder blocks, wherein each encoder block and decoder block comprises a convolution layer, a batch normalization layer, and a ReLu layer.

In non-limiting embodiments or aspects, the machine-learning model comprises a dropout layer arranged at an output of each encoder block and decoder block, the dropout layer configured to output a mean and a variance for each encoder block and decoder block. In non-limiting embodiments or aspects, the dropout layer is configured to estimate the mean and the variance based on at least two iterations. In non-limiting embodiments or aspects, wherein generating the 3D model comprises: filtering uncertain segmentation results based on segmentation maps and uncertainty maps output by the machine-learning model. In non-limiting embodiments or aspects, wherein filtering comprises: calculating an average uncertainty value for each segmented object; and filtering by class based on an uncertainty threshold determined based on a predictive mean and a predictive variance output by the machine-learning model. In non-limiting embodiments or aspects, wherein determining the insertion location based on the 3D model comprises: detecting a bifurcation point in the object in the 3D model; detecting a caudal end of a segmented ligament; determining an insertion region between the bifurcation point and the caudal end of the segmented ligament; and determining the insertion location on the object based on a plurality of total site scores generated for different points along the object. In non-limiting embodiments or aspects, the at least one object comprises at least one of the following: arteries, veins, ligaments, nerves, bones, muscle, lesions, foreign bodies, or any combination thereof. In non-limiting embodiments or aspects, the 3D model comprises uncertainty values. In non-limiting embodiments or aspects, wherein a plurality of points on the 3D model corresponds to an associated uncertainty value stored external to the 3D model.

Further non-limiting embodiments are set forth in the following clauses:

Clause 1: A method comprising: segmenting, with at least one computing device, an image of a sequence of images into at least one object based on machine-learning model configured to estimate its uncertainty for each segmentation; generating, with the at least one computing device, a 3D model of the at least one object; and determining, with the at least one computing device, an insertion location the at least one object based at least partially on an output of the machine-learning model.

Clause 2: The method of clause 1, further comprising collecting the sequence of images from a subject, each image in the sequence of images having spatial information.

Clause 3: The method of clauses 1 or 2, wherein determining the insertion location based at least partially on an output of the machine-learning model comprises determining the insertion location based at least partially on the 3D model, the 3D model generated based on the output of the machine-learning model and including having associated uncertainty values based on the output of the machine-learning model.

Clause 4: The method of any of clauses 1-3, wherein generating the 3D model is based at least partially on the output of the machine-learning model.

Clause 5: The method of any of clauses 1-4, wherein the machine-learning model is configured to output a predictive mean and a predictive variance.

Clause 6: The method of any of clauses 1-5, wherein the machine-learning model comprises encoder blocks and decoder blocks, wherein each encoder block and decoder block comprises a convolution layer, a batch normalization layer, and a ReLu layer.

Clause 7: The method of any of clauses 1-6, wherein the machine-learning model comprises a dropout layer arranged at an output of each encoder block and decoder block, the dropout layer configured to output a mean and a variance for each encoder block and decoder block.

Clause 8: The method of any of clauses 1-7, wherein the dropout layer is configured to estimate the mean and the variance based on at least two iterations.

Clause 9: The method of any of clauses 1-8, wherein generating the 3D model comprises: filtering uncertain segmentation results based on segmentation maps and uncertainty maps output by the machine-learning model.

Clause 10: The method of any of clauses 1-9, wherein filtering comprises: calculating an average uncertainty value for each segmented object; and filtering by class based on an uncertainty threshold determined based on a predictive mean and a predictive variance output by the machine-learning model.

Clause 11: The method of any of clauses 1-10, wherein determining the insertion location based on the 3D model comprises: detecting a bifurcation point in the object in the 3D model; detecting a caudal end of a segmented ligament; determining an insertion region between the bifurcation point and the caudal end of the segmented ligament; and determining the insertion location on the object based on a plurality of total site scores generated for different points along the object.

Clause 12: The method of any of clauses 1-11, wherein the at least one object comprises at least one of the following: arteries, veins, ligaments, nerves, bones, muscle, lesions, foreign bodies, or any combination thereof.

Clause 13: The method of any of clauses 1-12, wherein the 3D model comprises uncertainty values.

Clause 14: The method of any of clauses 1-13, wherein a plurality of points on the 3D model corresponds to an associated uncertainty value stored external to the 3D model.

Clause 15: A system comprising at least one computing device programmed or configured to: segment an image of a sequence of images into at least one object based on machine-learning model configured to estimate its uncertainty for each segmentation; generate, a 3D model of the at least one object; and determine an insertion location the at least one object based at least partially on an output of the machine-learning model.

Clause 16: The system of clause 15, wherein the at least one computing device is further programmed or configured to collect or receive the sequence of images from a subject, each image in the sequence of images having spatial information.

Clause 17: The system of clauses 15 or 16, wherein determining the insertion location based at least partially on an output of the machine-learning model comprises determining the insertion location based at least partially on the 3D model, the 3D model generated based on the output of the machine-learning model and including having associated uncertainty values based on the output of the machine-learning model.

Clause 18. The system of any of clauses 15-17, wherein generating the 3D model is based at least partially on the output of the machine-learning model.

Clause 19. The system of any of clauses 15-18, wherein the machine-learning model is configured to output a predictive mean and a predictive variance.

Clause 20. The system of any of clauses 15-19, wherein the machine-learning model comprises encoder blocks and decoder blocks, wherein each encoder block and decoder block comprises a convolution layer, a batch normalization layer, and a ReLu layer.

Clause 21. The system of any of clauses 15-20, wherein the machine-learning model comprises a dropout layer arranged at an output of each encoder block and decoder block, the dropout layer configured to output a mean and a variance for each encoder block and decoder block.

Clause 22. The system of any of clauses 15-21, wherein the dropout layer is configured to estimate the mean and the variance based on at least two iterations.

Clause 23. The system of any of clauses 15-22, wherein generating the 3D model comprises: filtering uncertain segmentation results based on segmentation maps and uncertainty maps output by the machine-learning model.

Clause 24. The system of any of clauses 15-23, wherein filtering comprises: calculating an average uncertainty value for each segmented object; and filtering by class based on an uncertainty threshold determined based on a predictive mean and a predictive variance output by the machine-learning model.

Clause 25. The system of any of clauses 15-24, wherein determining the insertion location based on the 3D model comprises: detecting a bifurcation point in the object in the 3D model; detecting a caudal end of a segmented ligament; determining an insertion region between the bifurcation point and the caudal end of the segmented ligament; and determining the insertion location on the object based on a plurality of total site scores generated for different points along the object.

Clause 26. The system of any of clauses 15-25, wherein the at least one object comprises at least one of the following: arteries, veins, ligaments, nerves, bones, muscle, lesions, foreign bodies, or any combination thereof.

Clause 27. The system of any of clauses 15-26, wherein the 3D model comprises uncertainty values.

Clause 28. The system of any of clauses 15-27, wherein a plurality of points on the 3D model corresponds to an associated uncertainty value stored external to the 3D model.

Clause 29: A computer program product comprising at least one non-transitory computer-readable medium including program instructions that, when executed by at least one computing device, cause the at least one computing device to: segment an image of a sequence of images into at least one object based on machine-learning model configured to estimate its uncertainty for each segmentation; generate, a 3D model of the at least one object; and determine an insertion location the at least one object based at least partially on an output of the machine-learning model.

Clause 30: The computer program product of clause 29, wherein the at least one computing device is further caused to collect or receive the sequence of images from a subject, each image in the sequence of images having spatial information.

Clause 31. The computer program product of clauses 29 or 30, wherein determining the insertion location based at least partially on an output of the machine-learning model comprises determining the insertion location based at least partially on the 3D model, the 3D model generated based on the output of the machine-learning model and including having associated uncertainty values based on the output of the machine-learning model.

Clause 32. The computer program product of any of clauses 29-31, wherein generating the 3D model is based at least partially on the output of the machine-learning model.

Clause 33. The computer program product of any of clauses 29-32, wherein the machine-learning model is configured to output a predictive mean and a predictive variance.

Clause 34. The computer program product of any of clauses 29-33, wherein the machine-learning model comprises encoder blocks and decoder blocks, wherein each encoder block and decoder block comprises a convolution layer, a batch normalization layer, and a ReLu layer.

Clause 35. The computer program product of any of clauses 29-34, wherein the machine-learning model comprises a dropout layer arranged at an output of each encoder block and decoder block, the dropout layer configured to output a mean and a variance for each encoder block and decoder block.

Clause 36. The computer program product of any of clauses 29-35, wherein the dropout layer is configured to estimate the mean and the variance based on at least two iterations.

Clause 37. The computer program product of any of clauses 29-36, wherein generating the 3D model comprises: filtering uncertain segmentation results based on segmentation maps and uncertainty maps output by the machine-learning model.

Clause 38. The computer program product of any of clauses 29-37, wherein filtering comprises: calculating an average uncertainty value for each segmented object; and filtering by class based on an uncertainty threshold determined based on a predictive mean and a predictive variance output by the machine-learning model.

Clause 39. The computer program product of any of clauses 29-38, wherein determining the insertion location based on the 3D model comprises: detecting a bifurcation point in the object in the 3D model; detecting a caudal end of a segmented ligament; determining an insertion region between the bifurcation point and the caudal end of the segmented ligament; and determining the insertion location on the object based on a plurality of total site scores generated for different points along the object.

Clause 40. The computer program product of any of clauses 29-39, wherein the at least one object comprises at least one of the following: arteries, veins, ligaments, nerves, bones, muscle, lesions, foreign bodies, or any combination thereof.

Clause 41. The computer program product of any of clauses 29-40, wherein the 3D model comprises uncertainty values.

Clause 42. The computer program product of any of clauses 29-41, wherein a plurality of points on the 3D model corresponds to an associated uncertainty value stored external to the 3D model.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

Additional advantages and details are explained in greater detail below with reference to the non-limiting, exemplary embodiments that are illustrated in the accompanying drawings, in which.

DETAILED DESCRIPTION

Figure 1:
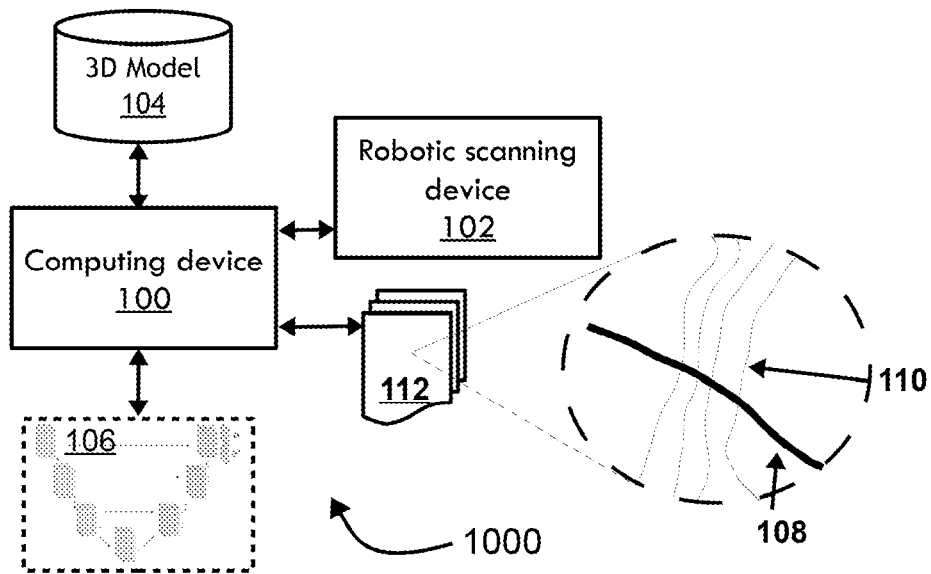
FIG. 1 illustrates a system for determining a needle injection site according to non-limiting embodiments.

It is to be understood that the embodiments may assume various alternative variations and step sequences, except where expressly specified to the contrary. It is also to be understood that the specific devices and processes described in the following specification are simply exemplary embodiments or aspects of the disclosure. Hence, specific dimensions and other physical characteristics related to the embodiments or aspects disclosed herein are not to be considered as limiting. No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Also, as used herein, the terms "has," "have," "having," or the like are intended to be open-ended terms. Further, the phrase "based on" is intended to mean "based at least partially on" unless explicitly stated otherwise.

As used herein, the term "computing device" may refer to one or more electronic devices configured to process data. A computing device may, in some examples, include the necessary components to receive, process, and output data, such as a processor, a display, a memory, an input device, a network interface, and/or the like. A computing device may be a mobile device. A computing device may also be a desktop computer or other form of non-mobile computer. In non-limiting embodiments, a computing device may include an artificial intelligence (AI) accelerator, including an application-specific integrated circuit (ASIC) neural engine such as Apple's M1® "Neural Engine" or Google's TENSORFLOW® processing unit. In non-limiting embodiments, a computing device may be comprised of a plurality of individual circuits.

In non-limiting embodiments, provided are systems, methods, and computer program products for determining a needle injection site with a multi-class Bayesian segmentation network that significantly reduces the risks associated with percutaneous procedures. Non-limiting embodiments provide for automated and/or semi-automated processes for identifying an optimal needle insertion location using robotics. Further, non-limiting embodiments provide for a portable solution that can be used in a wide variety of medical scenarios, leveraging computer vision with ultrasound imaging (or other medical imaging). In examples using ultrasound, the portability of the system described herein allows for the robot and system to be transported to different locations for serving emergency medical purposes.

Non-limiting embodiments utilize a novel and unique Bayesian deep learning-based multi-class temporal segmentation network for building a three-dimensional (3D) model of the tissue in the femoral region, which the system uses to determine the safest location for needle insertion such that the risk of complications will be lowered. Non-limiting embodiments may also determine a safe needle insertion location in other regions. Further, non-limiting embodiments provide for 3D heat map models depicting needle insertion safety levels, along with uncertainty-based pruning of noisy segmentations. Non-limiting embodiments allow for a robot to collect ultrasound images on both smooth and curved surfaces while being able to simultaneously segment arteries, veins, ligaments, nerves, bones, muscle, lesions, foreign bodies, and/or other objects/regions/anatomy/pathology/trauma/etc. Thus, non-limiting embodiments may be partially implanted in real-time or near-real-time, as scanning is being performed, and other non-limiting embodiments may be performed after scanning is completed using stored images.

FIG. 1 shows a system 1000 for determining a needle injection site 110 with a multi-class Bayesian segmentation network 106. A computing device 100 may be in communication with a robotic scanning device 102 that captures a sequence of images of a subject. For example, the robotic scanning device 102 may capture ultrasound images by automatically moving an ultrasound probe on the surface of a subject (e.g., a medical patient or the like). In non-limiting embodiments, the robotic scanning device 102 may be a robotic arm with a probe arranged on an end. In non-limiting embodiments, the robotic scanning device 102 may move at a controlled velocity and maintain consistent contact with the surface of the subject (e.g., at a known or measured force). In some non-limiting embodiments, the sequence of images may already be captured and stored by a robot or a human such that a robotic scanning device 102 is not used.

With continued reference to FIG. 1, the computing device 100 includes and/or is in communication with a Bayesian segmentation network 106. The Bayesian segmentation network 106 may be configured to segment each image of the sequence of images to classify (e.g., label) each object of a plurality of objects. In non-limiting embodiments, the Bayesian segmentation network may be in a U-Net architecture including a plurality of encoder blocks and decoder blocks. The objects for segmentation may include anatomical landmarks, such as but not limited to arteries, veins, ligaments, nerves, and/or the like. Based on the output of the model 106, the computing device may generate a 3D model of one or more of the objects of the plurality of objects and store the 3D model in the 3D model database. Based on the 3D model and the detected geometry of the objects, the computing device calculates an optimal insertion point of a needle injection site 110. The insertion point may be output as one or more images 112 annotated to show where, on a target vessel, a needle should be inserted. In some non-limiting embodiments, a robotic device may be used to automatically insert a needle based on the outputted optimal insertion point.

Figure 3:
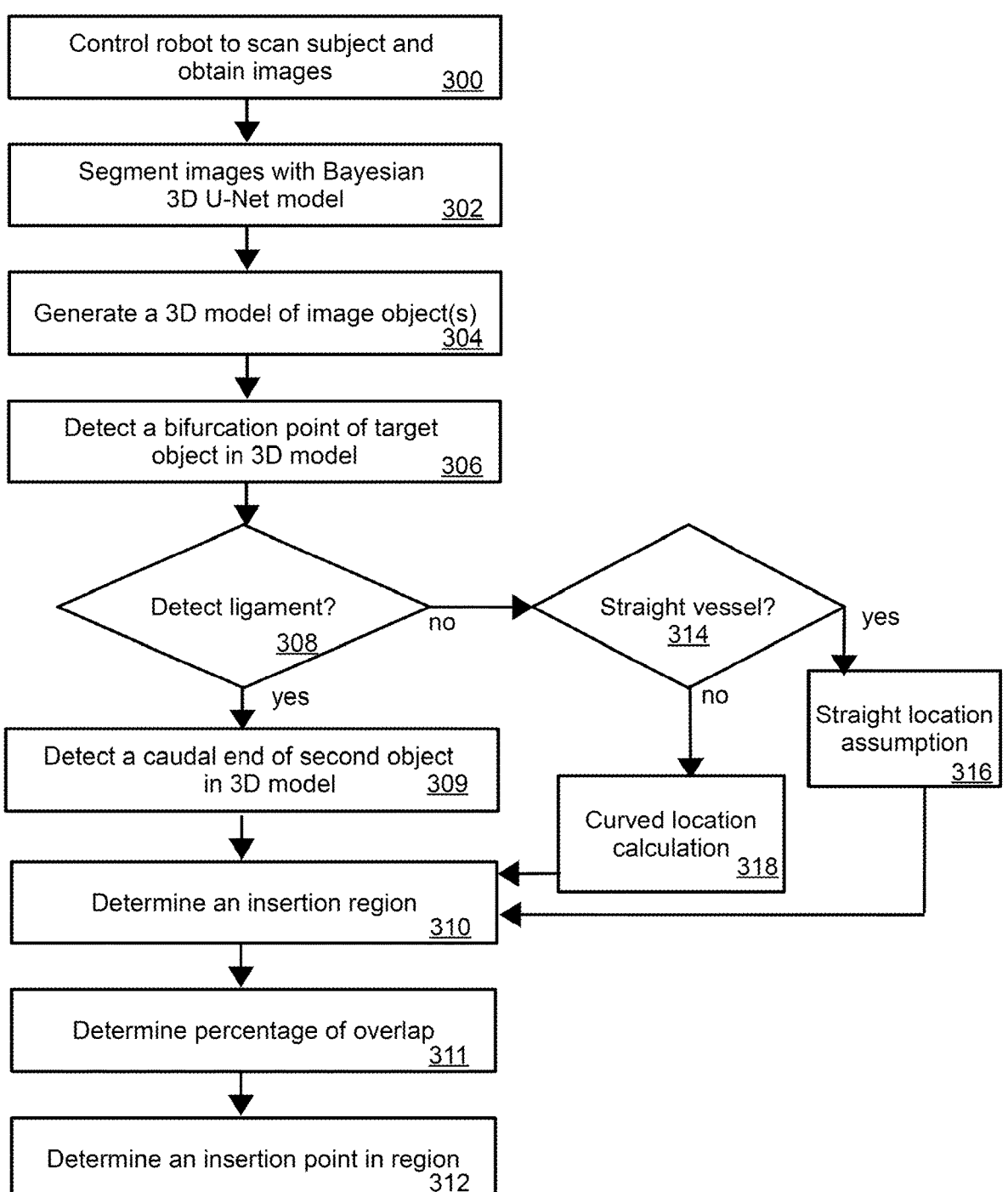
FIG. 3 illustrates a flow diagram for a method of determining a needle injection site according to non-limiting embodiments.

Referring now to FIG. 3, a flow diagram is shown for a method of determining a needle injection site 110 with a multi-class Bayesian segmentation network according to non-limiting embodiments. The steps shown in FIG. 3 are for example purposes only. It will be appreciated that additional, fewer, different, and/or a different order of steps may be used in non-limiting embodiments. At a first step 300, a robot is controlled to scan a subject and obtain a sequence of images. For example, the robot may scan the skin surface of a subject with an ultrasound probe to capture a region of the subject. In non-limiting embodiments, the robot applies a consistent force for acoustic coupling, patient comfort, and avoidance of excess pressure distorting tissue. This may help prevent disruption of the segmentation. In non-limiting embodiments, the robot is driven by velocity commands. To maintain a constant force, a velocity is applied along the direction of the ultrasound probe. The applied velocity (e.g., along the y-direction), $v_y$, is proportional to the difference between desired force, $f_d$, and the actual force measurement, f, from the sensor, as shown in equation 1:

$$v_y = -K_f * (f - f_d) \qquad \text{(Eq. 1)}$$

The position of the robot may be controlled in non-limiting embodiments by manually defining the start and end points of the scanning motion. The start and end positions are chosen to maximize the anatomical landmark coverage during scanning. The velocity values $v_{x,z}$ are computed with the following feedback control law:

$$v_{x,z} = K_{x,z}(p_{x,z} - p^*_{x,z}) \qquad \text{(Eq. 2)}$$

In the above equation, $K_{x,z}$ is the feedback controller gain for motion in the x- and z-directions, and $p_{x,z}$ and $p^*_{x,z}$ are the current and goal locations, respectively, in the xz-plane (which is normal to the scanning device, such as an ultrasound probe). The velocity of the end effector of the robot arm is then converted to the target joint velocity, which in turn is sent to the robot.

At step 302 of FIG. 3, the images may be segmented with a Bayesian 3D U-Net model. The images input into the Bayesian model may be captured by the robot during step 300. In other non-limiting embodiments, the images may have been previously captured by a human operator or robot and stored in a data storage device. In non-limiting embodiments, a 3D U-Net encoder-decoder architecture (e.g., as shown in FIG. 4) is configured as a Bayesian model.

Figure 4:
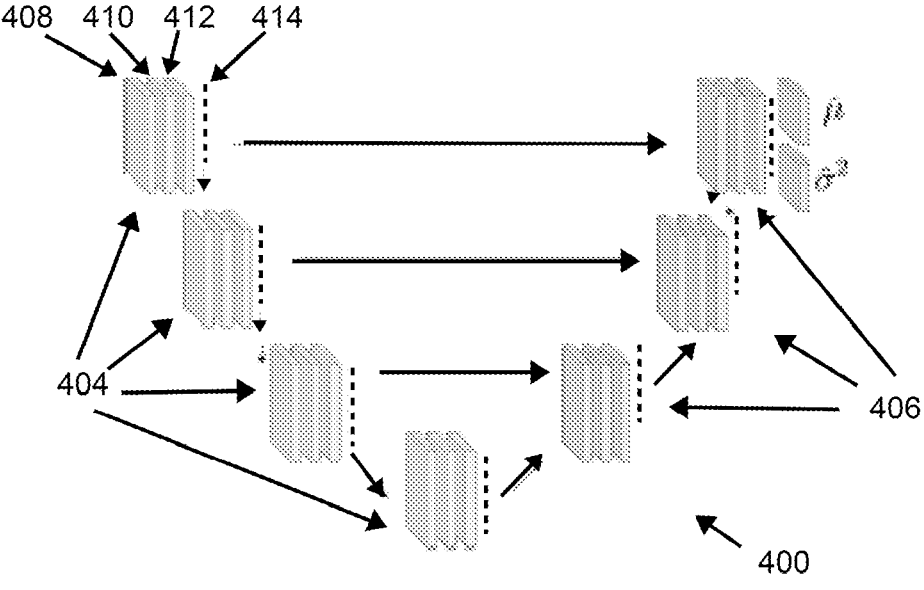
FIG. 4 illustrates a model network architecture according to non-limiting embodiments.

Referring to FIG. 4, in non-limiting embodiments a convolutional neural network 400 may be configured with a downsampling branch including a plurality of encoder blocks 404 and an upsampling branch including a plurality of decoder blocks 406. Although non-limiting embodiments may use any number of layers and encoder/decoder blocks, in some non-limiting embodiments, to limit memory usage, the encoder-side of the network is comprised of only four encoder blocks 404 and the decoder-side of the network is comprised of three encoder-paired decoder blocks 406. In non-limiting embodiments, each encoder block may include a convolution layer 408, a batch normalization layer 410, and a ReLu layer 412. Other layers may be included in other non-limiting embodiments. The network is configured as a Bayesian network by applying a distribution of values over the weights of each encoder and decoder block by adding a dropout function 414 at the output of each encoder and decoder block (thereby creating an ensemble of models from the above distribution). For example, each encoder block 404 may have a dropout applied to only the output of the ReLu layer 412, rather than to the output of each layer (e.g., the convolution layer 408 and the batch normalization layer 410). Similarly, each decoder block 406 may also have a dropout applied to only one layer as shown. The output of the Bayesian model is computed from the outputs of its ensemble of models drawn from its distribution of weights. For each pixel or region, a predictive mean ($\hat{\mu}$) output and a predictive variance ($\hat{\sigma}^2$) of that output is calculated across the ensemble of models, which can be represented as:

$$[\hat{\mu}, \hat{\sigma}^2] = f^{\hat{W}}(x) \tag{Eq. 3}$$

In Equation 3, f is the Bayesian 3D U-Net and is parameterized by model weights $\hat{W}$. The model may be trained using a stochastic cross entropy loss function.

The predictive mean and predictive variance are used to generate epistemic uncertainty maps that represent the model's uncertainty in its segmentation outputs. The mean and variance are obtained using test-time (or inference mode) stochastic forward passes, also referred to as Monte Carlo dropout represented as:

$$\frac{1}{T}\sum_{t=1}^{T}(\hat{\mu}_t - \overline{\mu})^{\otimes 2} \tag{Eq. 4}$$

In Equation 4, T is the total number of Monte Carlo samples and:

$$\overline{\mu} - \sum_{t=1}^{T}\frac{\hat{\mu}_t}{T}$$

Despite not actively using the logits variance output, $\hat{\sigma}^2$, for computing the aleatoric uncertainty, having the variance output may still be beneficial, due in part to the statistical uncertainty inherent in the data. Without the logits variance output, the epistemic uncertainty tends to overcompensate for that fact and results in poorer performance.

In non-limiting embodiments, to further account for variability in ultrasound imaging and other types of imaging, data augmentation may be applied to the image data prior to training the model. Data augmentations may include, but are not limited to, rotations, translations, flips (e.g., up-down and left-right), zooms (e.g., in and out), filtering, blurring, and combinations thereof. Various methods may be used for training the model. In non-limiting embodiments, an Adam optimizer is used along with a learning rate value of 0.0001, a sequence length of 8 frames, and a batch size of 8. It will be appreciated that various other values may be used. Further, in non-limiting embodiments, a resolution of 256× 256 pixels is used for the image dimensions. For obtaining the epistemic uncertainty maps, T=2 Monte Carlo samples may be used due to time constraints.

With continued reference to FIG. 3, at step 304, a 3D model is generated of one or more of the objects based on the output of the model in step 302. For example, upon obtaining the segmentation and uncertainty maps from the model, a 3D model of the objects (e.g., anatomical landmarks) in the scanned region is generated, and noisy segmentations are filtered out. In non-limiting embodiments, to filter out false-positive segmentation results, the following algorithm may be used: (1) calculate the average uncertainty values, $v_i$, within every segmentation contour, and (2) filter $v_i$ by class, c, and calculate uncertainty thresholds, $\tau_c$, with:

$$\tau_c = \hat{v}_c + \hat{\sigma}_c * \delta \tag{Eq. 5}$$

In Equation 5, $\hat{\mu}_c$ and $\hat{\sigma}_c$ are the average and standard deviation, respectively, of $v_i$ taken for class c, and $\delta$ is a manually tuned parameter representing the number of standard deviations away from the mean to filter out. A PERT statistical distribution may be used to determine an approximation to the uncertainty values $v_i$.

To obtain the coordinates for plotting with respect to the robot's fixed base frame, $^{ro}P_{im/px}$, the series of transformations is applied to the segmented ultrasound image as follows:

$$^{ro}P_{im/px} = {}^{ro}T_{tr} * {}^{tr}R_{im/mm} * {}^{im/mm}S_{im/px} * {}^{p}_{im/px} \tag{Eq. 6}$$

In Equation 6, $P_{im/px}$ is the segmented region in the image, $^{im/mm}S_{im/px}$ is the scaling factor to convert from pixel to millimeter (mm) units, $^{tr}T_{im/mm}$ is the transformation matrix to put the mm units into respect with the ultrasound transducer's frame, and $^{ro}T_{tr}$ is the transformation relation applied to place the points from the ultrasound transducer's frame into the robot's fixed base frame. $^{tr}T_{im/mm}$ is obtained from a manual calibration procedure and $^{ro}T_{tr}$ is obtained from the tfRobot Operating System (ROS) package.

In non-limiting embodiments in which images are captured without the use of a robotic device, such as the use of a hand-held scanner, plotting the coordinates may be performed with respect to another reference frame. For example, if using a hand-held scanner and a head-mounted augmented reality (AR) display, the system may plot coordinates with respect to the AR coordinate system by computing transformations from the output of the ultrasound tracking system. It will be appreciated that other variations are possible and that different devices and/or systems may be used to collect images.

In non-limiting embodiments, a color-coding schema may be applied to the 3D model for purposes of display. For example, arteries may be red, veins may be blue, ligaments may be green, and nerves may be yellow.

With continued reference to FIG. 3, at steps 306-310, an optimal needle insertion point for a target vessel is determined. The target vessel may be, for example, the femoral artery, femoral vein, or other vessels and/or tissues. The ideal site for femoral arterial puncture is generally accepted to be over the femoral head, below the inguinal ligament, and above the femoral arterial bifurcation. More specifically, it is advantageous to insert the needle up to 75% of the way down from the top of the femoral head, hence being closer to the arterial bifurcation (e.g., where the inguinal ligament and arterial bifurcation are approximately 33% and 100% from the top of the femoral head, respectively). Even in cases where medical practitioners are aware of the arterial bifurcation point through ultrasound imaging, they often go at least 1 cm cranially (e.g., in the superior direction). To further account for noise in the segmentation outputs, segmentation predictions may be filtered out for each class c removing segmentation predictions that have pixel-areas smaller than $\varphi_c$ pixels. As an example, the values 100, 300, and 1000 may be used for $\varphi_{artery}$, $\varphi_{vein}$, and $\varphi_{ligament}$, respectively. The aforementioned values were determined through empirical trials with manually collected ultrasound images.

At step 306, the bifurcation point of the femoral artery is detected. In non-limiting embodiments, this may be performed by searching for a gap of at least size g between contours from the objects classified as arteries in the 3D model. The location with the smallest gap may be identified as the point of bifurcation (point α). To account for noise in the segmentation results, the point may be confirmed by determining that at least γ % of the contours caudal to that point also contain a count of at least 2. The values of g and γ may be empirically determined to be, for example, 1 and 95, respectively.

At step 308, in non-limiting embodiments, it is determined if a ligament (or a specific ligament, such as the inguinal ligament) is detected. A different second object (e.g., an object other than the target vessel) may be detected additionally or alternatively. If a ligament is detected in the segmented objects, the method proceeds to step 309 and the caudal end of the ligament is detected. If a ligament is not detected in the segmented objects, the method proceeds to step 314. At step 314, it is determined if the first object (e.g., femoral artery) follows a straight path or if it has a gradual curve. If it follows a straight path, the method proceeds to step 316 in which the system assumes the ligament's location to be immediately off the cranial edge of the scan. If it follows a gradual curve, the method proceeds to step 318, in which the system iterates over each arterial contour at index i and calculates the angles between vectors u and v, with opposing endpoints at i–k and i+k, respectively, using the following: $\cos \theta = (u_k, v_k)/|u_k||v_k|$. The location of the ligament is then assumed to be at index i with the smallest angle θ as the ligament landmark, which may be referred to as point λ. To account for noise in the segmentation results, the point may be confirmed by determining that at least γ % of the contours caudal to that point also contain a count of at least 1.

At step 310 of FIG. 3, an insertion region is determined. A safe region may be identified between the two objects (e.g., femoral artery and inguinal ligament) by shifting α and λ toward each other by $\delta_\alpha$ % and $\delta_\lambda$ %, respectively. These shifted safe boundaries may be denoted as $\alpha_s$ and $\lambda_s$, respectively. This accounts for noise in the deep learning segmentation outputs. In non-limiting embodiments, a value of 15 may be used for $\delta_\alpha$ and $\delta_\lambda$, accounting for the 1 cm minimum distance to the arterial bifurcation given an average common femoral artery (CFA) segment length of 7 cm. It will be appreciated that various values and measurements may be used based on the type of subject (e.g., human or other animal), type of procedure, and/or the like.

At step 311 of FIG. 3, the percentage of overlap between the femoral artery (e.g., target vessel) and femoral vein is determined. This determination may include calculating the percentage of overlapping pixels when viewing the contours from a posterior angle. The overlap may be represented as $V_o$.

At step 312 of FIG. 3, the optimal needle insertion location is determined. In non-limiting embodiments, a proximity hazard score ($P_h$) is determined as:

$$P_h(\zeta) = \begin{cases} \dfrac{\sigma_\alpha}{1 + \|\zeta - \alpha\|_2} + \dfrac{\sigma_\lambda}{1 + \|\zeta - \lambda\|_2} & \text{if } \zeta \in [\lambda_s, \alpha_s] \\ \infty, & \text{otherwise} \end{cases} \quad \text{(Eq. 7)}$$

$$T_s = P_h + V_o$$

In Equation 7, $\zeta$ is the 3D coordinate for the center of an arterial segmentation contour, and $\sigma_\alpha$ and $\sigma_\lambda$ are values for weighing the importance of sufficient distance from α and λ, respectively. Arterial contours not within the safe region determined in step 310 or of an area smaller than $\varphi_{artery}$ are assigned a maximum score. The Total Site Score, $T_s$, is then obtained by adding $P_h$ and $V_o$ together, taking into account overflow and underflow. To select the final insertion location, the artery corresponding to the lowest value of $T_s$ is selected. If there are multiples of such values, the largest sized artery cross section is selected. To enhance clinical viability and explainability, a second 3D model may be generated in non-limiting embodiments illustrating a heat map of $T_s$. The heat map may be generated as described with respect to step 304, except with the following color encoding scheme: non-artery/vein structures and regions with values of infinity may be colored with an RGB value (128,128, 128), which is grey, and arteries may be shaded with RGB values of (255,η,η) where η=min($T_s$–min($T_s$)>255, 255). As a result, regions with higher values of $T_s$ appear white, whereas lower values appear bright red. The algorithm may be implemented using vectorized NumPy library methods, as an example. It will be appreciated that various color schemes, algorithms, and implementations may be used.

Figure 5:
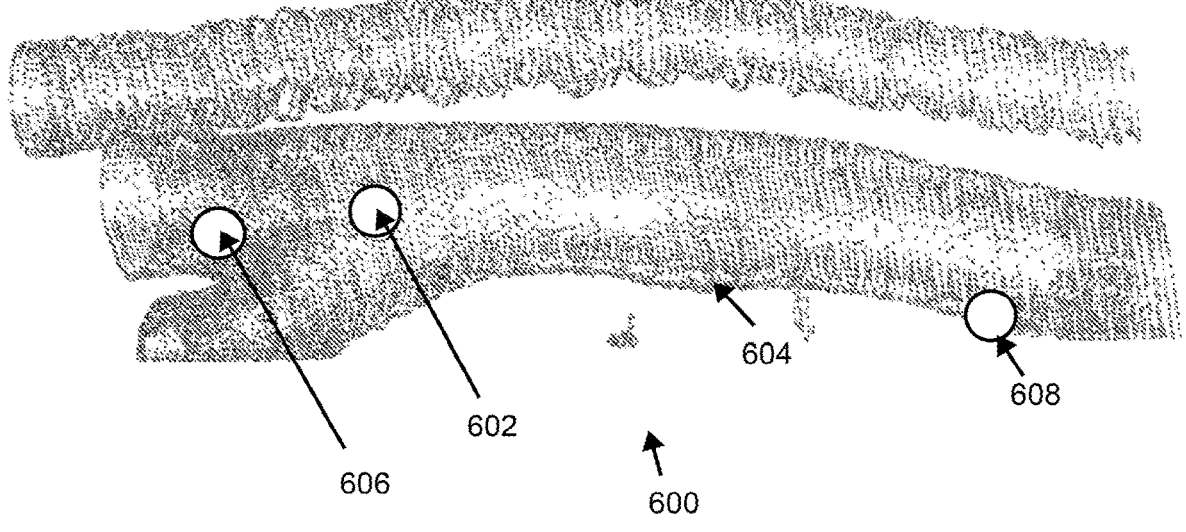
FIG. 5 illustrates a 3D model showing a needle injection site according to non-limiting embodiments.

FIG. 5 shows a 3D model 600 of a femoral artery 604, where point 602 represents the optimal insertion point determined at step 312 of FIG. 3. Point 606 represents the detected arterial bifurcation point and point 608 represents the detected ligament. In non-limiting embodiments in which a heat map is also generated based on the total site scores, the heat map may colorize the region of the artery 604 between point 602 and point 608 with a gradient going from grey (toward point 608) to bright red (toward point 602), representing a gradual change from "unsafe" to "safe".

Figure 6:
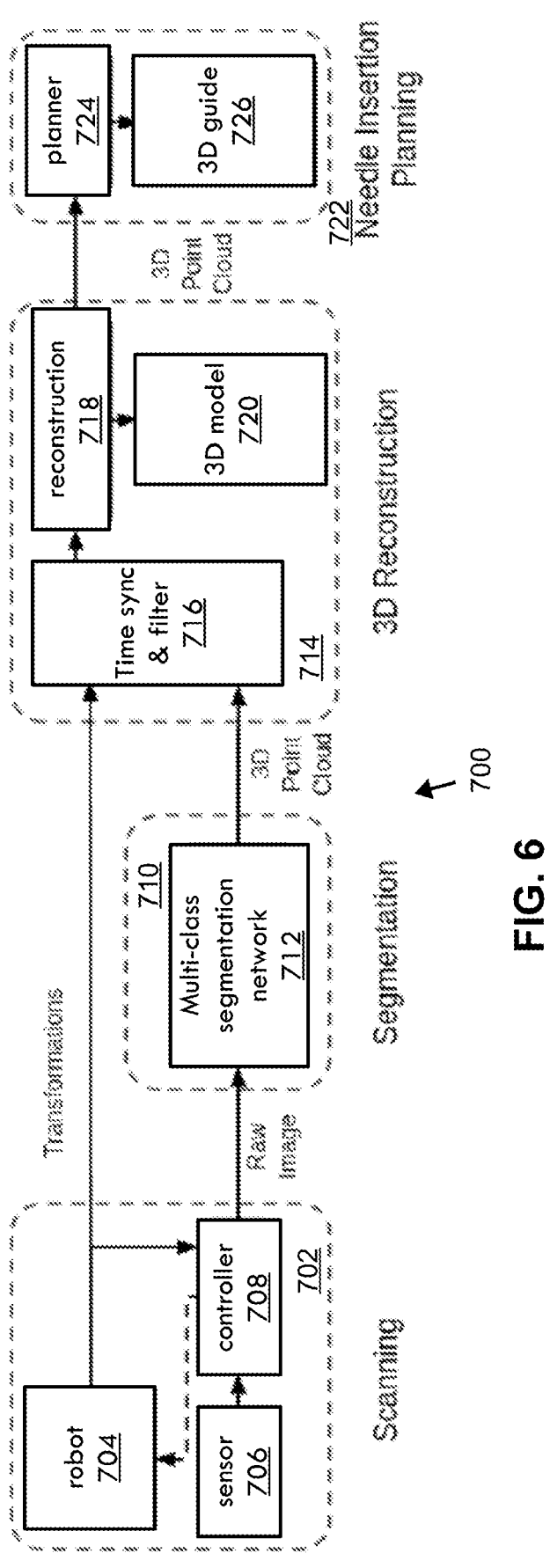
FIG. 6 illustrates an automated or semi-automated pipeline according to non-limiting embodiments.

Referring now to FIG. 6, an automated robotic pipeline 700 is shown according to non-limiting embodiments. The pipeline 700 may be automated with no or minimal human intervention. The pipeline includes a scanning phase 702, a segmentation phase 710, a 3D reconstruction phase 714, and a needle insertion planning phase 722. In the scanning phase 702, a controller 708 (e.g., a hybrid force-position controller) may receive the output of a force sensor 706 and positional information from the ROS or other like platform, and calculate the target joint velocity for controlling a robotic arm 704 to scan a subject. The robotic arm 704 or other robotic device may scan a subject with an ultrasound sensor, as an example, to obtain a sequence of images. The robotic arm 704 may be controlled as described with respect to step 300 of FIG. 3, as an example. The raw (e.g., unprocessed) images may be output by the controller 708 and sent to a segmentation phase 710 of the pipeline 700.

The raw images are processed with a multi-class segmentation network 712, such as the Bayesian 3D U-Net model described herein. The images may be segmented as described with respect to step 302 of FIG. 3, as an example. The multi-class segmentation network 712 may output segmentation and uncertainty maps for the processed images. Based on the model output, the coordinates of the segmented objects may be determined and output (e.g., as 3D point cloud data or the like) to be processed in the 3D reconstruction phase 714 of the pipeline 700.

In the 3D reconstruction phase 714, the coordinates output by the network 712 and kinematic data (e.g., obtained from ROS or other like platform) are synchronized and filtered. This may be performed by a time synchronization and filter module 716, which may, as an example, use the Approximate TimeSynchronizer class in ROS. The module 716 also receives the transformations calculated based on Equation 6, which are applied to the pixel coordinates. The filtered coordinates may be formed into 3D point cloud data by a 3D reconstruction module 718, which generates a 3D model 720 based on the point cloud data and outputs the point cloud data to the needle insertion planning phase 722.

The final point cloud data may represent global coordinates and may be completed upon completion of the scanning. A needle insertion planner module 724 may process the 3D model to generate a 3D guide 726 that visually represents the arterial bifurcation point, optimal insertion point, and other objects (e.g., ligaments and/or the like). The needle insertion planner module 724 may process the 3D model as described in steps 306, 308, 310, 311, 312, 314, 316, 318 of FIG. 3, as an example.

Figure 2:
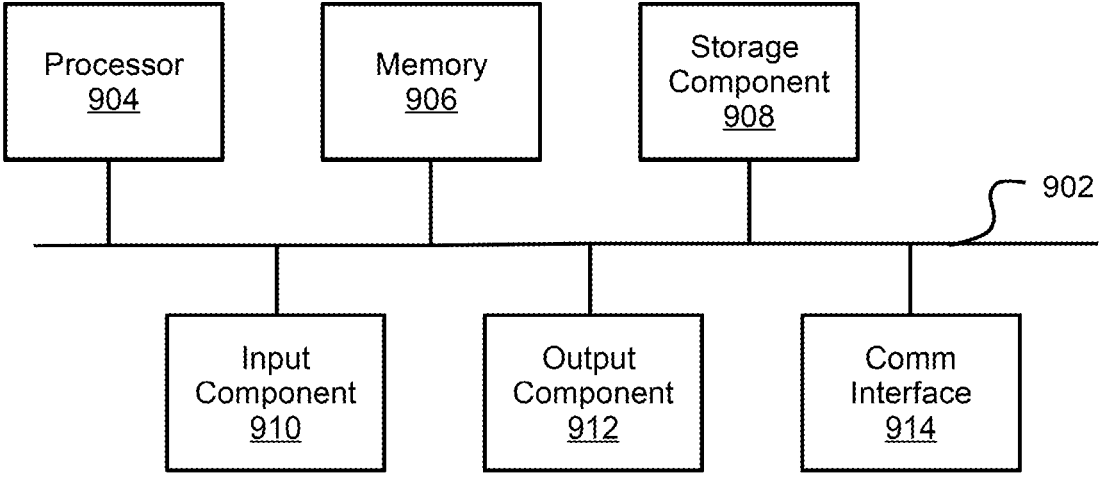
FIG. 2 illustrates example components of a computing device used in connection with non-limiting embodiments.

Referring now to FIG. 2, shown is a diagram of example components of a computing device 900 for implementing and performing the systems and methods described herein according to non-limiting embodiments. In some non-limiting embodiments, device 900 may include additional components, fewer components, different components, or differently arranged components than those shown. Device 900 may include a bus 902, a processor 904, memory 906, a storage component 908, an input component 910, an output component 912, and a communication interface 914. Bus 902 may include a component that permits communication among the components of device 900. In some non-limiting embodiments, processor 904 may be implemented in hardware, firmware, or a combination of hardware and software. For example, processor 904 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 906 may include random access memory (RAM), read only memory (ROM), and/or another type of dynamic or static storage device (e.g., flash memory, magnetic memory, optical memory, etc.) that stores information and/or instructions for use by processor 904.

With continued reference to FIG. 2, storage component 908 may store information and/or software related to the operation and use of device 900. For example, storage component 908 may include a hard disk (e.g., a magnetic disk, an optical disk, a magneto-optic disk, a solid state disk, etc.) and/or another type of computer-readable medium. Input component 910 may include a component that permits device 900 to receive information, such as via user input (e.g., a touch screen display, a keyboard, a keypad, a mouse, a button, a switch, a microphone, etc.). Additionally, or alternatively, input component 910 may include a sensor for sensing information (e.g., a global positioning system (GPS) component, an accelerometer, a gyroscope, an actuator, etc.). Output component 912 may include a component that provides output information from device 900 (e.g., a display, a speaker, one or more light-emitting diodes (LEDs), etc.). Communication interface 914 may include a transceiver-like component (e.g., a transceiver, a separate receiver and transmitter, etc.) that enables device 900 to communicate with other devices, such as via a wired connection, a wireless connection, or a combination of wired and wireless connections. Communication interface 914 may permit device 900 to receive information from another device and/or provide information to another device. For example, communication interface 914 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 900 may perform one or more processes described herein. Device 900 may perform these processes based on processor 904 executing software instructions stored by a computer-readable medium, such as memory 906 and/or storage component 908. A computer-readable medium may include any non-transitory memory device. A memory device includes memory space located inside of a single physical storage device or memory space spread across multiple physical storage devices. Software instructions may be read into memory 906 and/or storage component 908 from another computer-readable medium or from another device via communication interface 914. When executed, software instructions stored in memory 906 and/or storage component 908 may cause processor 904 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software. The term "programmed or configured," as used herein, refers to an arrangement of software, hardware circuitry, or any combination thereof on one or more devices.

Although embodiments have been described in detail for the purpose of illustration, it is to be understood that such detail is solely for that purpose and that the disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A method comprising:

segmenting, with at least one computing device, an image of a sequence of images into at least one object based on a machine-learning model configured to estimate its uncertainty for each segmentation;

generating, with the at least one computing device, a 3D model of the at least one object by filtering uncertain segmentation results based on segmentation maps and uncertainty maps output by the machine-learning model, wherein filtering comprises:

calculating an average uncertainty value for each segmented object; and filtering by class based on an uncertainty threshold determined based on a predictive mean and a predictive variance output by the machine-learning model; and determining, with the at least one computing device, an insertion location of the at least one object based at least partially on an output of the machine-learning model.

2. The method of claim 1, further comprising collecting the sequence of images from a subject, each image in the sequence of images having spatial information.

3. The method of claim 1, wherein determining the insertion location based at least partially on an output of the machine-learning model comprises determining the insertion location based at least partially on the 3D model, the 3D model generated based on the output of the machine-learning model and including having associated uncertainty values based on the output of the machine-learning model.

4. The method of claim 1, wherein generating the 3D model is based at least partially on the output of the machine-learning model.

5. The method of claim 1, wherein the machine-learning model is configured to output a predictive mean and a predictive variance.

6. The method of claim 1, wherein the machine-learning model comprises encoder blocks and decoder blocks, wherein each encoder block and decoder block comprises a convolution layer, a batch normalization layer, and a ReLu layer.

7. The method of claim 6, wherein the machine-learning model comprises a dropout layer arranged at an output of each encoder block and decoder block, the dropout layer configured to output a mean and a variance for each encoder block and decoder block.

8. The method of claim 7, wherein the dropout layer is configured to estimate the mean and the variance based on at least two iterations.

9. The method of claim 1, wherein determining the insertion location based on the 3D model comprises:

detecting a bifurcation point in the object in the 3D model;

detecting a caudal end of a segmented ligament;

determining an insertion region between the bifurcation point and the caudal end of the segmented ligament; and determining the insertion location on the object based on a plurality of total site scores generated for different points along the object.

10. The method of claim 1, wherein the at least one object comprises at least one of the following: arteries, veins, ligaments, nerves, bones, muscle, lesions, foreign bodies, or any combination thereof.

11. The method of claim 1, wherein the 3D model comprises uncertainty values.

12. The method of claim 1, wherein a plurality of points on the 3D model corresponds to an associated uncertainty value stored external to the 3D model.

13. A system comprising at least one computing device programmed or configured to:

segment an image of a sequence of images into at least one object based on a machine-learning model configured to estimate its uncertainty for each segmentation;

generate a 3D model of the at least one object; and determine an insertion location of the at least one object based at least partially on an output of the machine-learning model by:

detecting a bifurcation point in the object in the 3D model;

detecting a caudal end of a segmented ligament;

determining an insertion region between the bifurcation point and the caudal end of the segmented ligament; and determining the insertion location on the object based on a plurality of total site scores generated for different points along the object.

14. The system of claim 13, wherein the at least one computing device is further programmed or configured to collect or receive the sequence of images from a subject, each image in the sequence of images having spatial information.

15. The system of claim 13, wherein determining the insertion location based at least partially on an output of the machine-learning model comprises determining the insertion location based at least partially on the 3D model, the 3D model generated based on the output of the machine-learning model and including having associated uncertainty values based on the output of the machine-learning model.

16. The system of claim 13, wherein the machine-learning model comprises encoder blocks and decoder blocks, wherein each encoder block and decoder block comprises a convolution layer, a batch normalization layer, and a ReLu layer.

17. The system of claim 13, wherein the machine-learning model comprises a dropout layer arranged at an output of each encoder block and decoder block, the dropout layer configured to output a mean and a variance for each encoder block and decoder block.

18. The system of claim 17, wherein the dropout layer is configured to estimate the mean and the variance based on at least two iterations.

19. A computer program product comprising at least one non-transitory computer-readable medium including program instructions that, when executed by at least one computing device, cause the at least one computing device to:

segment an image of a sequence of images into at least one object based on a machine-learning model configured to estimate its uncertainty for each segmentation;

generate, a 3D model of the at least one object by filtering uncertain segmentation results based on segmentation maps and uncertainty maps output by the machine-learning model, wherein filtering comprises:

calculating an average uncertainty value for each segmented object; and filtering by class based on an uncertainty threshold determined based on a predictive mean and a predictive variance output by the machine-learning model; and determine an insertion location of the at least one object based at least partially on an output of the machine-learning model.

* * * * *